US008796217B2

(12) United States Patent
Amari et al.

(10) Patent No.: US 8,796,217 B2
(45) Date of Patent: Aug. 5, 2014

(54) USE OF TRANSESTERIFIED OLIVE OIL IN THE COSMETIC FIELD

(75) Inventors: Sergio Amari, Paderno d' Adda (IT); Alain Thibodeau, Quebéc (CA)

(73) Assignee: Hallstar Italia S.R.L., Milan (IT)

( * ) Notice: Subject to any disclaimer, the term of this patent is extended or adjusted under 35 U.S.C. 154(b) by 638 days.

(21) Appl. No.: 12/864,076

(22) PCT Filed: Oct. 21, 2008

(86) PCT No.: PCT/IB2008/054327
§ 371 (c)(1),
(2), (4) Date: Oct. 13, 2010

(87) PCT Pub. No.: WO2009/093104
PCT Pub. Date: Jul. 30, 2009

(65) Prior Publication Data
US 2011/0021439 A1    Jan. 27, 2011

(30) Foreign Application Priority Data

Jan. 25, 2008  (IT) .............................. MI2008A0118
Apr. 16, 2008  (IT) .............................. AN2008A0020

(51) Int. Cl.
| | |
|---|---|
| A61P 17/00 | (2006.01) |
| C11C 3/04 | (2006.01) |
| C10L 1/19 | (2006.01) |
| A61K 8/92 | (2006.01) |

(52) U.S. Cl.
CPC .............. *A61K 8/922* (2013.01); *A61Q 169/00* (2013.01)
USPC ............ 514/18.8; 514/18.6; 530/207; 44/308

(58) Field of Classification Search
None
See application file for complete search history.

(56) References Cited

U.S. PATENT DOCUMENTS

| | | | |
|---|---|---|---|
| 2,333,093 | A | 11/1943 | Dearborn |
| 3,288,824 | A | 11/1966 | Gattefosse et al. |
| 4,927,464 | A | 5/1990 | Cowie |
| 5,075,331 | A | 12/1991 | Lang et al. |
| 5,227,169 | A | 7/1993 | Heiber et al. |
| 5,260,336 | A | 11/1993 | Forse et al. |
| 5,314,685 | A | 5/1994 | Tyle et al. |
| 5,502,076 | A | 3/1996 | Dixit et al. |
| 5,527,523 | A | 6/1996 | Laruelle et al. |
| 5,653,970 | A | 8/1997 | Vermeer |
| 5,770,185 | A | 6/1998 | Wachter et al. |
| 5,968,528 | A | 10/1999 | Deckner et al. |
| 6,017,549 | A | 1/2000 | Knight et al. |
| 6,140,435 | A | 10/2000 | Zanotti-Russo |
| 6,143,307 | A | 11/2000 | Maurin |
| 6,488,946 | B1 | 12/2002 | Milius et al. |
| 6,500,440 | B1 | 12/2002 | Chi et al. |
| 7,736,662 | B2 * | 6/2010 | Amari et al. .................. 424/401 |
| 2001/0006665 | A1 | 7/2001 | Auguste |
| 2007/0264210 | A1 * | 11/2007 | Robinson ........................ 424/59 |

FOREIGN PATENT DOCUMENTS

| | | |
|---|---|---|
| DE | 43 38 591 | 5/1995 |
| EP | 0 589 843 | 3/1994 |
| FR | 2 377 193 | 8/1978 |
| FR | 2 634 120 | 1/1990 |
| FR | 2 832 057 | 5/2003 |
| GB | 450 368 | 7/1936 |
| WO | WO 94/18292 | 8/1994 |
| WO | WO 95/13261 | 5/1995 |
| WO | WO 99/29814 | 6/1999 |
| WO | WO 00/00174 | 1/2000 |
| WO | WO 0203929 A1 | 1/2002 |
| WO | WO 03/032943 | 4/2003 |

OTHER PUBLICATIONS

Amari, 2004, SOFW-Journal, vol. 130, 1-5.*
Sundar Raj Applied Microbiology, May 1965, vol. 13, No. 3.*
Panthenol-Website: http://web.archive.org/web/20090927004228/http://www.ehow.com/about_5403302_benefits-panthenol.html, 4 pages retrieved on Oct. 7, 2013.*
International Search Report dated Jun. 24, 2010 issued in corresponding PCT Application No. PCT/IB2008/054327.
B&T S.r.l.: "Olivem 1000—Product Literature," Quetzal Quimica SRL, Nov. 2002, pp. 1-10 (XP002580798).
A. Amari, Ch. Schubert: "A New Fucntional Ingredient able to build up fluid system on the basis of Olive Oil," SÖFW-Journal, vol. 130, Apr. 2004, pp. 1-5 (XP002580799).
H. Trommer, R.H.H. Neubert: "Overcoming the Stratum Corneum: The Modulation of Skin Penetration," Skin Pharmacology and Physiology, vol. 19, May 9, 2006 (XP002580800).
R. Celades et al.: "preparation des esters de polyoxyethyleneglycols par glycolyse" Proceedings of the IVth International Congress on Surface Active Substances, Brussels, Sep. 7-12, 1964, vol. 1, pp. 249-255, XP008026227 *table p. 253*.
Rigano et al. (Olivem 900: Make up e skin care. Cosmetic News 1999; XXII (126): 211-5).
Database WPI, Section Ch, Week 200168 Derwent Publications Ltd., London, GB, AN 2001-600663, XP002231217 & KR 2001 038 071 A (Pacific Ind Co), May 15, 2001.
Database CA 'Online! Chemical Abstracts Service, Columbus, Ohio, US; Arcos, Jose A et al: "Quantitative enzymic production of 1,6-diacyl sorbitol esters" retrieved from STN Database accession No. 129:274734 XP002231216 Abstract -& Biotechnology and Bioengineering (1998), 60(1), 53-60, XP002231214.
Coternon A., et al.:, "Reactions of Olive Oil and Glycerol over Immobilized Lipases", JAOCS, vol. 75, No. 5, 1998, pp. 657-660, XP001135083, experimental procedures p. 658.

(Continued)

*Primary Examiner* — Satyanarayana R Guidibande
(74) *Attorney, Agent, or Firm* — Kenyon & Kenyon LLP

(57) ABSTRACT

The use of transesterified olive oil for increasing the penetration rate of cosmetically-active and/or dermatologically-active ingredients or as cosmetic moisturizer is disclosed.

6 Claims, 4 Drawing Sheets

(56) References Cited

OTHER PUBLICATIONS

Umbach W.:, "Kosmetik: Entwicklung, Herstellung und Anwendung kosmetischer Mittel", 1988, Georg Thieme Verlag, Stuttgart XP002231215, p. 510, paragraph 2—p. 511, paragraph 2.
Quantitative Enzymatic Production of 1,6-Diacyl Sorbitol Esters, Jose A. Arcos et al.:, XP-002231216-, p. 53-60.
Preliminary Amendment dated Jul. 23, 2003 in U.S. Appl. No. 10/466,909.
Office Action dated Dec. 9, 2005 in U.S. Appl. No. 10/466,909.
Amendment dated Apr. 10, 2006 in U.S. Appl. No. 10/466,909.
Supplemental Amendment dated May 31, 2006 in U.S. Appl. No. 10/466,909.
Office Action dated Jun. 28, 2006 in U.S. Appl. No. 10/466,909.
Interview Summary dated Sep. 22, 2006 in U.S. Appl. No. 10/466,909.
Amendment dated Sep. 28, 2006 in U.S. Appl. No. 10/466,909.
Advisory Action dated Oct. 25, 2006 in U.S. Appl. No. 10/466,909.
Amendment dated Mar. 28, 2007 in U.S. Appl. No. 10/466,909.
Office Action dated Jul. 2, 2007 in U.S. Appl. No. 10/466,909.
Amendment dated Jan. 2, 2008 in U.S. Appl. No. 10/466,909.
Office Action dated Apr. 15, 2008 in U.S. Appl. No. 10/466,909.
Amendment dated Jul. 29, 2008 in U.S. Appl. No. 10/466,909.
Advisory Action dated Aug. 19, 2008 in U.S. Appl. No. 10/466,909.
Office Action dated Feb. 3, 2009 in U.S. Appl. No. 10/466,909.
Response dated Aug. 3, 2009 in U.S. Appl. No. 10/466,909.
Notice of Allowance dated Nov. 24, 2009 in U.S. Appl. No. 10/466,909.

\* cited by examiner

USE OF TRANSESTERIFIED OLIVE OIL IN THE COSMETIC FIELD

CROSS-REFERENCE TO RELATED APPLICATIONS

This application is a 371 National Phase Application to International Application No.: PCT/IB2008/054327, filed Oct. 21, 2008, which claims priority to MI2008A000118, filed Jan. 25, 2008 and AN2008A000020, filed Apr. 16, 2008, the entire disclosure of which is hereby incorporated by reference.

FIELD OF THE INVENTION

This invention refers to the use of transesterified olive oil in the cosmetic field for the improvement of skin-penetration properties.

BACKGROUND OF THE INVENTION

The problem of making an active ingredient penetrate in the skin is of dramatic importance in cosmetics and, maybe even more, in dermatology. Natural penetration of most active ingredients, however, often has rates which may render the action of the active ingredient less effective or even fully ineffective. In order to overcome this, it is useful to find an agent which, by embedding in itself an active ingredient, causes it to penetrate in the skin at a greater rate than its natural rate, so that the effect is full and timely. Thereby, in many cases it would also be possible to reduce the concentration of active ingredient, thereby reducing to a minimum any possible side effects. In principle a delivery enhancement could also allow the use of active ingredients that otherwise have to be chemically transformed in order to be able to go through the stratum corneum. The problem with penetration improvement agents of this type is that they have to provide such acceleration, without interacting significantly with the active ingredient, so as not to invalidate the action thereof, nor damage the properties thereof.

One way might be the addition to the cosmetic product of small amounts of toxic substances, which, by killing some cells, would reduce penetration resistance. This way, however, risks damaging the skin irreversibly and is therefore to be avoided.

Also the application of moisturisers requires good skin penetration properties. Skin hydration and the variation thereof are often correlated with skin health and skin appearance. The lack of normal skin hydration is hence often associated with potentially serious cosmetic concerns and may cause distress and even skin disorders. There are two mechanisms of physiological modulation by the skin: 1) the natural humidifying factor and 2) the intercellular lipidic layers, located between keratinocytes. Said keratinocytes, being lipophilic, prevent excessive water evaporation through the epidermis. Although epidermal keratinocytes and the lipidic intercellular layers determine the barrier function of the skin, the lipidic compartment plays a predominant role. The normal physiological barrier function of the epidermis is hence based on highly regular laminae, into which intercellular lipids penetrate. As a matter of fact, in the epidermal stratum corneum, intercellular lipids are integrated in laminar gel phases and in laminar liquid crystals.

The most commonly used methods for modulating skin hydration consist in the topic application of emollients or humectants.

Emollients provide partial occlusion of the pores and may soften, humidify and improve the appearance of the stratum corneum of the skin.

On the other hand, humectants are generally hygroscopic molecules, such as for example urea or glycerol, capable of binding with atmospheric humidity, and they help keep skin water in balance.

Neither emollients nor humectants, however, affect the integrity of the barrier function of the skin.

In general, the skin lies on the surface of the body and serves as a sheath for the protection of inner organs, preventing them from coming into direct contact with the environment. In any case, the skin is extremely complex and has both intracrinous and paracrinous capabilities. Thus, the skin protects from UV radiation (melanogenesis), provides immune protection and has a barrier function which prevents the penetration of foreign particles. It is also dynamically involved in the management of the inner levels of water. It is also the seat of vitamin D photoproduction and of the distribution of vitamin E, introduced nutritionally.

The main skin layers are the dermis and the epidermis. The dermis is the site of the synthesis of the extracellular components, such as collagen, elastin and the glycosaminoglycans which are produced and secreted by the dispersed, resident fibroblastic cells. On the other hand, epidermal cell density is much higher and is represented predominantly by keratinocytes. The epidermis renews itself constantly through an outward flow and the differentiation of cells which originate from the epidermal stratum basale up to the stratum corneum (SC). The stratum corneum, the outermost layer of the epidermis, supplies most of the permeability barrier, which is mainly supplied by the organised embedding of keratinocytes into an extra-cellular matrix rich in lipids.

Chemical analyses have shown that the intercellular lipids of the stratum corneum consist mainly of ceramides, cholesterol, cholesterol esters and fatty acids, themselves being synthesised by keratinocytes. The three-dimensional organisation of those lipids has been the subject of various studies with the suggestion of various different models (Madison, 2003). In a recent model (Norlén, 2001), it has been suggested that the fats of the stratum corneum (mortar) exist in the form of a crystalline gel, arranged as multi-laminar system which is found among keratinocytes (bricks). A way to visualise the organisation of the lipids of the stratum corneum and the keratinocytes is to imagine a brick wall wherein the bricks representing keratinocytes are neatly juxtaposed and chelated in lipidic layers of mortar. The integrity of cell components is well-known and, in particular, the lipidic layers of the stratum corneum must necessarily maintain barrier function integrity. The destruction of the barrier function of the stratum corneum will lead to an increase of trans-epidermal water loss and to a consequent reduction in the level of skin hydration, with the negative consequences already illustrated above.

In addition to intercellular lipidic laminae (crystalline gel), other classes of lipids originating from sebum also play an important role in the stratum corneum. The primary lipids found in sebum are: cholesterol, sterol and wax esters, triglycerides and squalene (Stewart, 1992). Triglycerides can be produced inside the sebaceous gland and be released in the form of free fatty acids. Following the deposition in the outer surface of the stratum corneum, the sebum fats (or the surface lipids of the skin) perform an anti-microbic action (Georgel, 2005; Willie, 2003), as transient antioxidants (alfa-tocopherol) (Thiele, 1999), as well as supplying important molecules having targeted, biological purposes. For example, glycerol, more likely obtained by hydrolysis of triglycerides, acts as hygroscopic agent and participates in the capability of retaining the water of the stratum corneum (Fluhr, 2003). Some fatty acids, such as oleic acid and linoleic acid, behave as binders of peroxysome-proliferator-activated receptors (PPARs). It has been shown that the activation of PPARs is involved in keratocyte differentiation (Komuves, 2000) and in restoring the accelerated barrier function which follows acute abrogation of the barrier (Schurer, 2002; Mao Qiang, 2004). Despite being secreted on the outer surface of the stratum corneum, the sebum fats may be remarkably affected in maintaining the integrity of the lipidic configuration of much deeper layers. A number of studies have proved that, depending on the categories of lipids, a gradient of sebaceous surface lipids of the skin is detected through the stratum corneum (Blanc, 1989; Norlén, 1998; Sheu, 1999; Thiele, 1999; Norlén, 2001; Yagi, 2007).

The epidermal mission of keratinocytes ends with the desquamation process. Keratinocyte (or corneocyte) exfoliation is a process necessary for epidermal renewal and may be obtained through the proteolytic action of various enzymes (Houben, 2007). It is suggested that the desquamation phenomenon may cause a certain degree of structural dis-organisation in the intercellular, lipidic laminar matrix of the stratum corneum (Norlén, 2001, Sheu, 1999). The exfoliation process could be represented as a destabilising operation which opens small gaps in the underlying lipidic matrix (in the same way as the removal of a brick from a wall should crush the surrounding mortar). Such micropores may become paths for the sebaceous lipids to mix with the lipidic counterpart of the stratum corneum. Intermixing of sebaceous lipids with those features of inner layers of the stratum corneum might then occur. Together, these studies have established the physiological importance of sebum products in the skin surface as well as for the entire epidermis.

The object of the present invention is that of designing high-penetration dermatological agents which, on the one hand, allow faster penetration of the active ingredients into the skin and, on the other hand, act as biomimetic restructuring agents. The present invention is mainly based on fatty acid compositions similar to those found in the skin for generating skin-compatible liquid crystals, so as to mimike the molecular organisation of the intercellular lipidic laminae of the stratum corneum. The liquid crystals thus formed must have the opportunity to cross skin layers at high speed as well as to integrate physiologically in the lipidic barrier of the skin and to strengthen the integrity thereof.

SUMMARY OF THE INVENTION

The objects set forth above are brilliantly achieved by the present invention, which refers to the use of transesterified olive oil in the cosmetic field for the improvement of skin-penetration properties.

BRIEF DESCRIPTION OF DRAWINGS

The present invention will now be illustrated in greater detail with reference to the accompanying drawings, wherein.

BEST WAY TO CARRY OUT THE INVENTION

Figure 1:
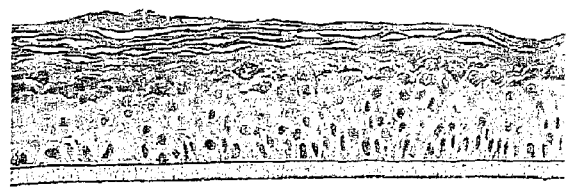
FIG. 1 shows the haematoxylin-eosin stain of a histological section of the RHE (epidermis—porous membrane)

Per se, olive oil is a mixture of fatty acid esters, varying according to its origin and to the type of olives employed for obtaining it, depending on years and on the processing method. However, since the percentages of the different esters vary within well-defined and widely-known ranges, although with a certain degree of variability, olive oil may be considered as a defined composition.

Olive oil transesterification may be performed by any alcohol or alcohol mixture, according to the normal procedures of organic chemistry. Particularly valid results have been obtained by performing the transesterification with cetearyl alcohol and/or sorbitol.

By performing olive oil transesterification with both these alcohols, a product identified according to the INCI nomenclature as cetearyl-olivate, sorbitan-olivate is formed. This product is found in the form of liquid crystals.

According to a particularly effective production process, olive oil firstly undergoes saponification, under usual conditions. The obtained fatty acids are then esterified, partly with cetearyl alcohol, partly with sorbitan, the obtained products being endly mixed together.

The Applicant has verified the effectiveness in transepidermal penetration of the skin-compatible liquid crystals generated by cetearyl-olivate, sorbitan-olivate, obtained by olive oil transesterification. This involves, on the one hand, the ability to withhold perspiration water, so as to obtain a strong hydrating effect and, on the other hand, that such crystals may be used to improve transepidermal penetration of biologically-active molecules.

Although the present invention refers to all the products which may be obtained by transesterifying olive oil, the ingredient (INCI: cetearyl-olivate, sorbitan-olivate) used in the following of the present exemplifying description is a complex combination of fatty acids, chemically related to the lipidic composition of the skin surface, which has the distinctive property of self-emulsifying in hydrophilic or lipophilic means. Cetearyl-olivate, sorbitan-olivate therefore represents a single biomimetic, restructuring agent which is entrusted with the double feature of 1) re-establishing and maintaining skin barrier integrity and 2) itself providing the emulsifying base. This leads to the creation of cosmetic formulations which are biologically functional with "physiologically" natural skin perception following application.

The peculiarity of these ingredients is that they consist of a combination of fatty acid which chemically—as well as physiologically—reproduces very well what has been found on the skin surface (Table 1), due to the similarity of these products with sebum. As mentioned previously, the fats of the skin surface (sebaceous fatty acids) have this ability of penetrating into the inner layers of the stratum corneum, of embedding in the intercellular lipidic laminar matrix of the stratum corneum and of becoming part of the barrier layer. Using a fatty acid composition which reproduces sebum, it therefore becomes possible to exploit the natural "entry card" thereof to access the inner layer of the stratum corneum. Therefore, by using olive oil as a starting material, the Applicant has succeeded in deriving the cosmetic ingredients, such as cetearyl-olivate, sorbitan-olivate, entrusted with a physiological action through the natural affinity thereof for the lipidic laminar system of the stratum corneum.

TABLE 1

Fatty acid composition of olive oil and of the skin surface lipids

| | Fatty Acid Concentration (%) | |
|---|---|---|
| | Olive Oil | Skin Surface |
| Non-saponifiable | 1.0-1.5 | 5.0 |
| Palmitic | 7.5-20 | 5.0 |
| Stearic | 0.5-5.0 | 20-28 |
| Oleic | 55-83 | 30-35 |
| Linoleic | 3.5-13.5 | 3.0-3.5 |
| Linolenic | max 0.8 | max 1.2 |
| Lauric | — | — |
| Myristic | <0.1 | — |

—: Below the level of detection

Figure 3:
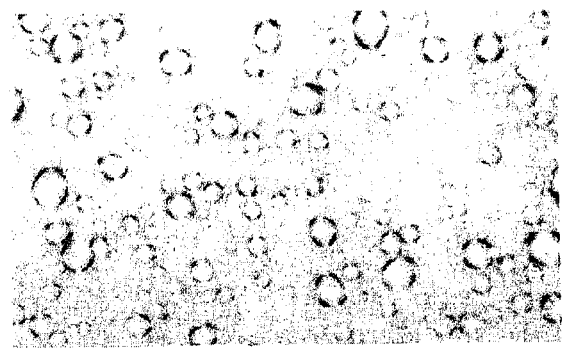
FIG. 3 is a scanning electron microscope (SEM) picture showing the liquid crystal structure of cetearyl-olivate, sorbitan-olivate.

In addition to having a single composition of fatty acid, the ingredient cetearyl-olivate, sorbitan-olivate adopts a liquid crystal configuration when it is emulsified, as highlighted in FIG. 3. Those liquid crystals have a molecular structure similar to the one observed in the lipidic laminae of the stratum corneum. As a matter of fact, the walls of the liquid crystals consist of alternate layers of fatty acids and water, therefore reproducing the standard intercellular lipidic matrix structure of the stratum corneum (Norlén, 2001). The biomimetism of cetearyl-olivate, sorbitan-olivate is therefore twofold 1) chemical mimetism with the lipidic composition of the skin surface and 2) structural mimetism with the intercellular, lipidic, laminar organisation of the stratum corneum. In the following, reference will be made to those structures formed by cetearyl-olivate, sorbitan-olivate, such as bio-compatible liquid crystals.

According to a first aspect, the skin-penetration properties of transesterified olive oil, together with the characteristic structure thereof, allow to embed into said structure cosmetically-active and/or dermatologically-active molecules, in order to be able to bring them into the innermost layers of the skin, obtaining a more marked and/or more timely effect.

According to a second aspect, transesterified olive oil as such, once penetrated into the innermost layers of the skin, is able to embed itself and act as a barrier, so as to avoid excessive evaporation of water through the skin, which leads to an optimal hydrating effect, devoid of any negative consequence.

It is evident that both aspects of the present invention are a direct consequence of the same phenomenon: the high penetration rate into the skin of transesterified olive oil.

The present invention will now be further illustrated based on the following, non-limiting examples.

Example 1

An in-vitro Reconstructed Human Epidermis (RHE) system has been used. As biologically-active molecule, caffeine was chosen. When it is applied to the RHE surface, caffeine has the ability of penetrating into the epidermal layers. Transepidermal penetration of caffeine may be quantified by using a radioactive marker. Caffeine may also be integrated in various formulations (emulsions) to verify the effect of said agent in improving the transepidermal penetration rate.

Human skin keratinocytes were dispersed on an artificial porous membrane and the differentiation of said keratinocytes was induced up to a phase reported as day 13. Reconstructed Human Epidermis (RHE) grows in a culture medium defined in a water-air interface environment. The histological organisation of the RHE is shown in FIG. 1 and shows a typical configuration of epidermis with a layer of stratum corneum.

RHE is arranged in plates having 12 wells each in the presence of 1 ml of maintenance medium at 37° C., 5% $CO_2$. The RHE in each well represented an individual experimental condition. Any substance applied to the tip of the RHE having the ability of penetrating transepidermally may be gathered in the culture medium below the RHE and quantified using suitable detection methods.

Different formulations were prepared according to Table 2. Cetearyl-olivate, sorbitan-olivate (Olivem 1000 Crystal Skin) was used as liquid crystal mould in various formulation environments (Table 2, A, B, and C). Control formulae were also verified (Table 2, D and E).

Radioactive caffeine ($^{14}$C-caffeine, 1 mCi/m, 0.04 mM added to 0.339 mM of cold caffeine) is used as marker. This mixture (in the following referred to as "caffeine", unless otherwise stated) is representative of a water-soluble, biologically-active molecule. Caffeine was tested pure or integrated in the various formulae. Caffeine was integrated in the formula with weak shaking and kept at room temperature overnight before the test.

TABLE 2

Sample composition

| | FORMULA (ingredient %) | | | | |
|---|---|---|---|---|---|
| INGREDIENT | A | B | C | D | E |
| Cetearyl-olivate (and) sorbitan-olivate | 5.0 | 5.0 | 5.0 | 0 | 0 |
| Ceteareth-20 | — | — | — | 2.0 | — |
| Cetearyl alcohol | — | — | — | 3.0 | — |
| Cetearyl alcohol and cetearyl glucoside | — | — | — | — | 5.0 |
| Cetyl-palmitate (and) sorbitan-palmitate (and) sorbitan-olivate | — | — | 2.5 | — | — |
| Ethylhexyl-olivate, oil of Olea Europaea (olive) (PROPOSED) | — | 2.0 | 2.0 | 2.0 | 2.0 |
| Oil of Simmondia Chinensis | — | 2.0 | 2.0 | 2.0 | 2.0 |
| Dicaprylyl-carbonate | — | 1.0 | 1.0 | 1.0 | 1.0 |
| Water | 95.0 | 90.0 | 87.5 | 90.0 | 90.0 |
| Preservative | 0.2 | 0.2 | 0.2 | 0.2 | 0.2 |

Formulae A, B, C, D or E or caffeine (control) pure were applied to the RHE surface in each well. All conditions were carried out in n=3. A kinetic sample was arranged on the culture medium below RHE with 7 kinetic times of 1, 2, 3, 4, 5, 6 and 24 hours. The radioactivity contained in the collected samples was measured using liquid scintillation. The results are expressed as cpm (counts per minute) of released caffeine and represent the relative concentration of caffeine in the epidermis.

Keratinocyte vitality was ascertained using the MTT assay: MTT salt (3-(4,5-dimetil-tiaol-2-il)-2,5 diphenyltetrazolium bromide) may be reduced through the mitochondrial enzyme succinate-dehydrogenase found in living cells. The reduction product, formazan crystals, may be quantified by optic density at 540 mm and is proportional to the number of living cells. The MTT assay was performed on the RHE at the 24 hour instant.

In these experimental conditions, the A, B, C and E formulations encouraged caffeine passage into the epidermis. The effects were statistically significant ($p<0.05$) compared to the control epidermis which received pure caffeine with no formulation. For example, at the 24 hour instant, only formulae A, B and C significantly increased caffeine penetration (p>0.01) compared to pure caffeine (control). The D and E formulae did not show a significant effect (p>0.05) compared to pure caffeine (control). It must be noted that the main ingredient of formula E (cetearyl alcohol and cetearyl glucoside) generates liquid crystals. These results prove that the chemical composition of liquid crystals generated by cetearyl-olivate, sorbitan-olivate (skin-compatible liquid crystals) is unique and important to significantly increase transepidermal penetration. Moreover, the penetration increase effect observed in this assay cannot be simply explained with a negative effect on cell vitality, since the results of the MTT assay show normal vitality (cell vitality 100%) (tab. 3).

TABLE 3 cell vitality for MTT assay

|  | Cell vitality (%) |
|---|---|
| Control (pure caffeine) | 100 |
| Formula A | 118 |
| Formula B | 114 |
| Formula C | 112 |
| Formula D | 97 |
| Formula E | 103 |

Example 2

Figure 2:
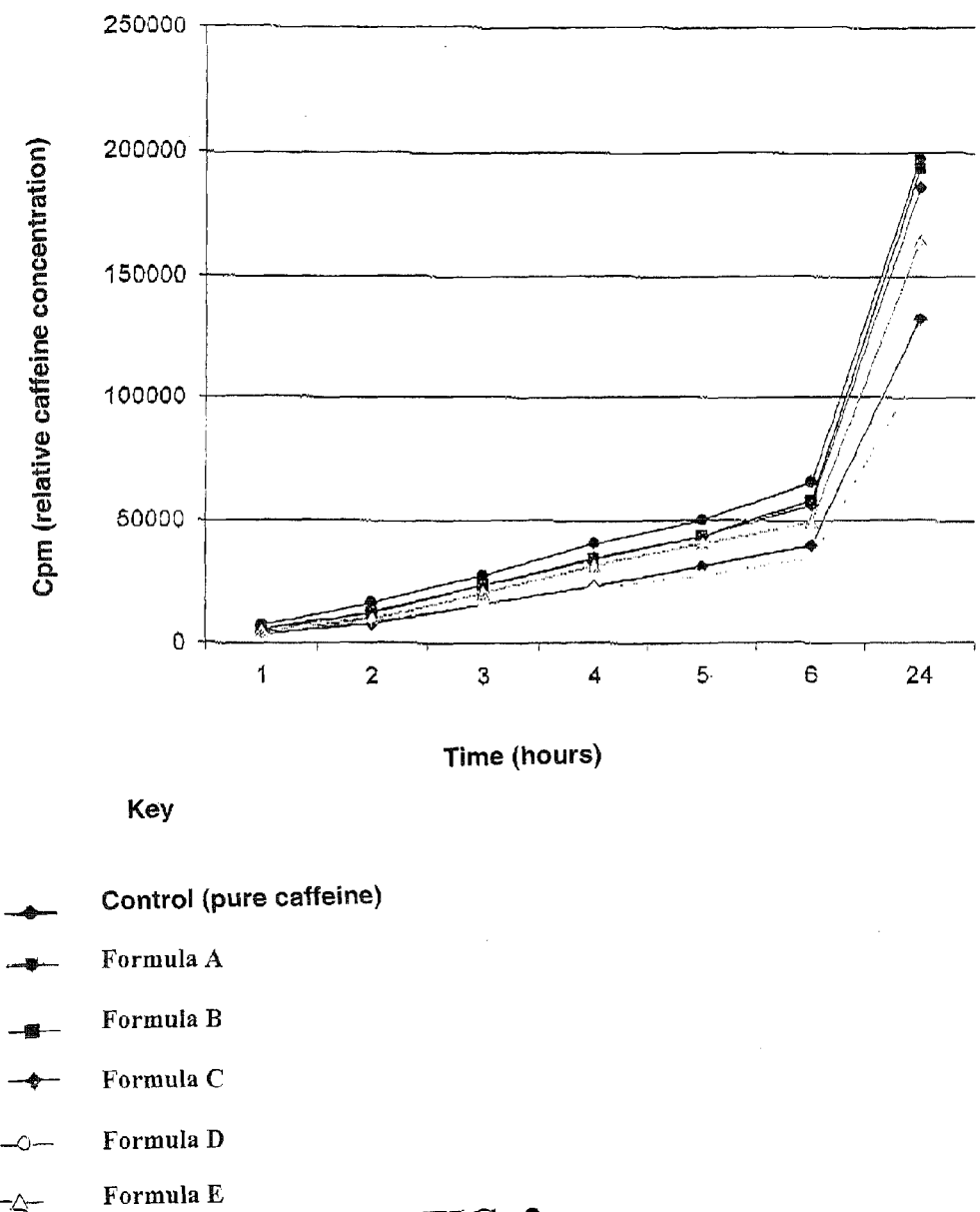
FIG. 2 shows the accumulation of caffeine on the other side of the porous membrane.
Figure 4:
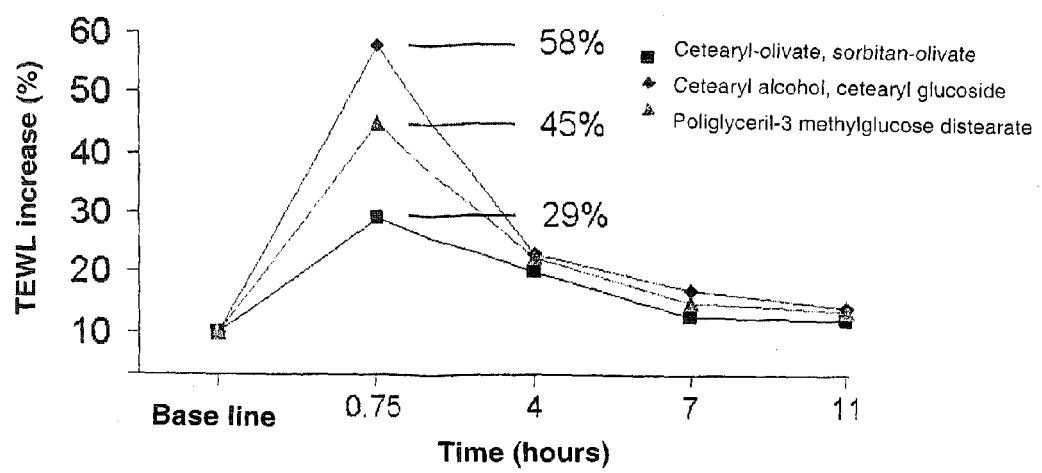
FIG. 4 is a diagram showing the effect of the presence of cetearyl-olivate, sorbitan-olivate and of other lipidic compositions on skin barrier integrity.

The clinical efficiency of bio-compatible liquid crystals generated by cetearyl-olivate, sorbitan-olivate was clinically verified. Firstly, its skin biocompatibility was verified in a study on its effect on transepidermal water loss (TEWL) with respect to other lipidic compositions. TEWL is a convalidated method for assessing the skin permeability barrier function (Fluhr, 2006). Ten volunteers have applied topically identical concentrations (5%) of the following ingredients: cetearyl-olivate, sorbitan-olivate; cetearyl alcohol, cetearyl-glucoside and poliglyceril-3 methylglucose distearate. The results—see FIG. 4—have shown that the application of cetearyl-olivate, sorbitan-olivate reduced the increase of TEWL by 29% over control formulae (FIG. 2).

These results support the need for a physiological compatibility between the topically-applied lipidic composition and the skin. Cetearyl alcohol, cetearyl-glucoside and poliglyceril-3 methylglucose distearate may be identified in categories as non-compatible lipidic compositions, due to the fact that they activate excessive water loss following application. This might be interpreted as a transient destabilisation of barrier integrity which leads to the forming of micropores through which water may come out. TEWL progressively regains base line values when barrier integrity is restored. The importance of the lipidic composition has been proven consisting of the appropriate, skin-compatible lipidic composition and ratio (Mao Qiang, 1995, De Paepe, 2002). The compatibility of cetearyl-olivate, sorbitan-olivate with the lipidic composition of the skin is detected by a relatively low level of induced TEWL. The lipidic composition of the ingredient applied to the skin seems to be of greater importance than the three-dimensional configuration formed. It has already been proven that cetearyl-olivate, sorbitan-olivate generates liquid crystals (FIG. 1). Interestingly, cetearyl alcohol and cetearyl glucoside also have the capability of forming liquid crystals when they are emulsified. Even though the advantages of liquid crystals are well-known in cosmetic formulations, only their chemical manufacture in terms of fatty acid composition will make them physiologically compatible with the skin. The results obtained with cetearyl-olivate, sorbitan-olivate clearly underline the importance not only of forming liquid crystal structures, but also of having them chemically compatible with the skin (they are quite similar) to provide the desired penetration and moisturising effect, maintaining optimal barrier integrity, which until today was not foreseeable on the basis of the prior art.

Example 3

Since the overall skin hydration level lies in a barrier function and in the water-retaining capability, the skin hydrating effect of cetearyl-olivate, sorbitan-olivate was compared to that of glycerine-employing corneometry. Glycerine is produced and secreted by sebaceous glands and acts as a natural skin humectant (Fluhr, 2003). Ten volunteers have applied a solution consisting of 2% glycerine and 0.4% xanthan gum and an emulsion of 4% cetearyl-olivate, sorbitan-olivate on different sites of the palm side of the forearm. As expected, the glycerine solution has produced a rapid increase of skin surface hydration, as can be seen in FIG. 5.

Figure 5:
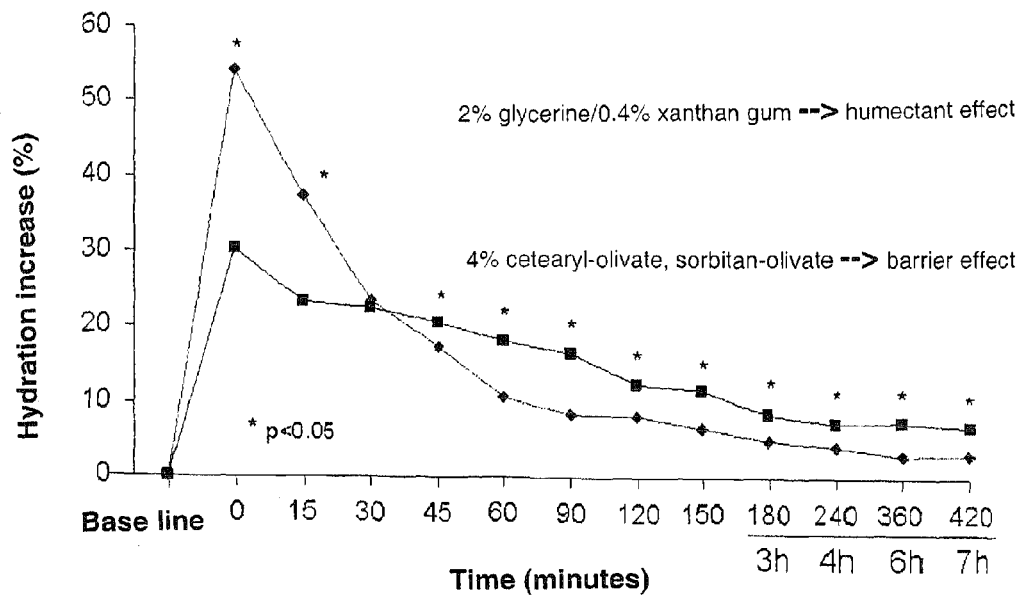
FIG. 5 is a diagram showing a comparison between the hydration properties of glycerine and of cetearyl-olivate, sorbitan-olivate.

The skin hydration peak shown in FIG. 5 progressively disappeared reaching significantly lower values than cetearyl-olivate, sorbitan-olivate from 45 minutes up to 7 hours after application. The cetearyl-olivate, sorbitan-olivate emulsion did not cause a transient peak in hydration, but resulted in a more stable long-term effect. This effect may be interpreted as a physiological penetration and as an integration of skin-compatible liquid crystals formed by cetearyl-olivate, sorbitan-olivate, thereby increasing the integrity of the stratum corneum. The "barrier" effect of cetearyl-olivate, sorbitan-olivate differs clearly from the humectant behaviour of glycerine. In a concerted action, glycerine as natural skin humectant and cetearyl-olivate, sorbitan-olivate as natural component of the stratum corneum barrier therefore can mutually integrate, for example in a hydration kit containing them both, activating two important complementary skin hydration mechanisms.

Example 4

The effectiveness of cetearyl-olivate, sorbitan-olivate was further clinically analysed for its functional hydration effect. Ten volunteers applied an emulsion consisting of cetearyl-olivate, sorbitan-olivate to one half of their face and Ceteareth-20, cetearyl alcohol to the other half, twice daily, for a period up to 45 days.

Figure 6:
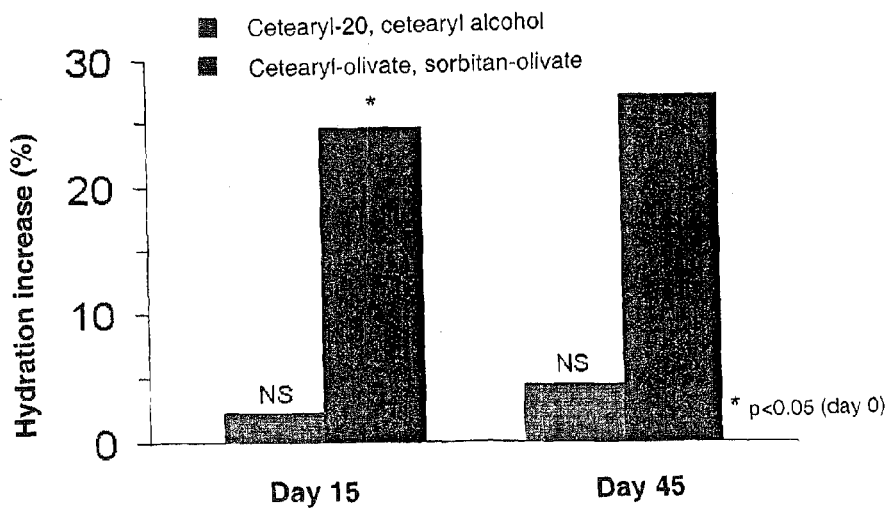
FIG. 6 is a diagram showing the functional effectiveness for skin hydration of cetearyl-olivate, sorbitan-olivate.

Skin hydration was boosted by 24.7% and by 27.3% after 15 days and 45 days, respectively (p<0.05), following the application of cetearyl-olivate, sorbitan-olivate, as shown in FIG. 6. The non-significant effects of 2.2% (day 15) and 4.5% (day 45) were observed with ceteareth-20, cetearyl alcohol as control. In parallel, the formulation containing 2.5% cetearyl-olivate, sorbitan-olivate raised by 40% the sensory perception level as judged by the same subjects. The results obtained in this test are consistent with an improved effect of the stratum corneum barrier following the application of skin-compatible liquid crystals formed by cetearyl-olivate, sorbitan-olivate, which lead to greater long-term hydration.

Skin homeostasis is based to a high degree on the integrity of the stratum corneum barrier, which consists of keratinocytes embedded in a matrix rich in lipids. The integrity thereof guarantees protection from environmental attacks and avoids excessive transepidermal water loss. The barrier function may be disrupted by noxious external agents, such as pollutants, strong detergents and aging factors which therefore affect the water evaporation rate, the level of skin sensitivity, and cellular functions. Finally, this may result in skin dryness, skin irritation and a weaker physiological response.

According to the invention, skin-compatible liquid crystals have been generated which mimic both the lipidic composition of the skin surface and the molecular organisation of the intercellular lipidic laminae of the stratum corneum. The liquid crystals of cetearyl-olivate, sorbitan-olivate have the property of integrating physiologically in the lipidic skin barrier. They act as biomimetic restructuring agents and restore the optimal integrity of the barrier function of the skin. Moreover, their similarity with the lipidic composition of the skin surface allows those liquid crystals to improve the sensory perception with part of the formulation.

Figure 7:
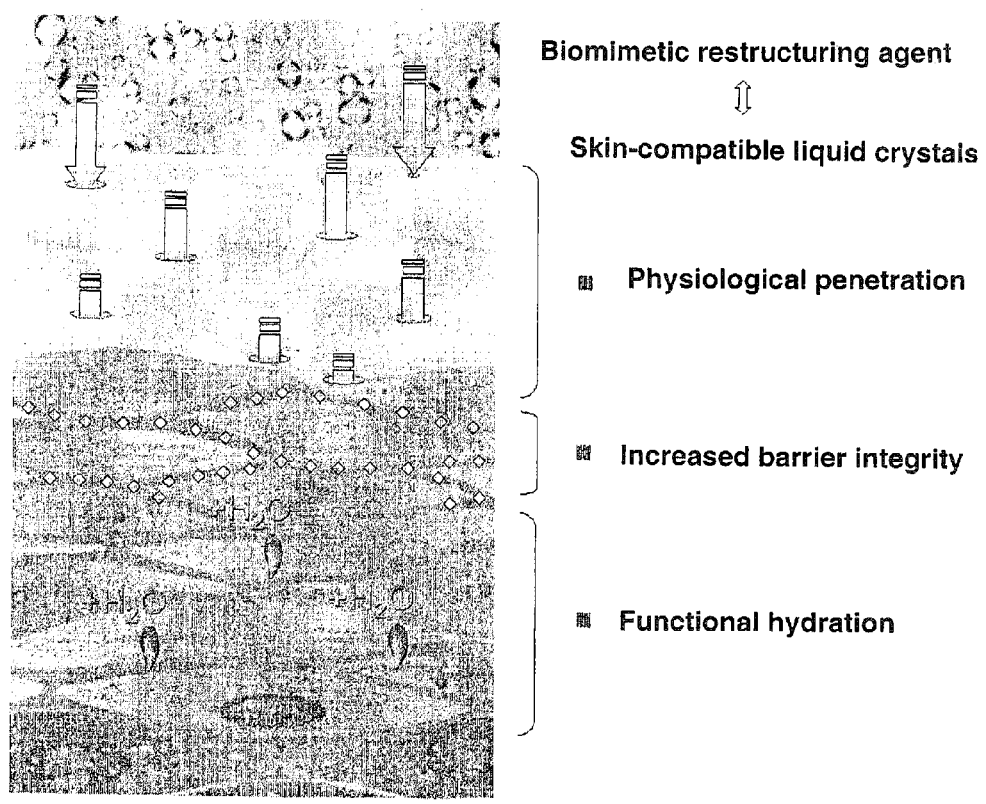
FIG. 7 is a picture of the mechanism of action of esters according to the present invention.

The suggested skin action of liquid crystals of cetearyl-olivate, sorbitan-olivate may be summed up in FIG. 7. When it is applied to the liquid crystal surface of the skin—due to their chemical compatibility with the surface lipidic composition—they should penetrate and settle in the upper layers of the stratum corneum, thereby strengthening the barrier function. The action of physiological and biomimetic restructuring of cetearyl-olivate, sorbitan-olivate provides improved barrier integrity and higher levels of skin water.

The dermatological compatibility of cetearyl-olivate, sorbitan-olivate makes it a key ingredient in the formulation of products which respect the chemical and structural homeostasis of the lipidic skin barrier and it is hence physiologically highly suitable. This dermatological compatibility also supports the physiological enhancement of delivery of actives through the epidermis.

The ability to cause active ingredients to penetrate in the skin has been verified with caffeine, but such property is displayed with any active ingredient, such as antioxidants, free-radical scavengers, hyaluronic acid, collagen, botulinum toxin, cortison-like drugs, antibiotics, chemotherapeutic agents, wound-healing drugs, peptides.

The invention claimed is:

1. A method of enhancing skin penetration of cosmetically-active or dermatologically-active ingredients in a cosmetic formulation comprising preparing a cosmetic formulation containing a transesterified olive oil and a cosmetically-active or dermatologically-active ingredient by:
   (a) emulsifying the transesterified olive oil to form a liquid crystal; and
   (b) embedding the cosmetically-active or dermatologically-active ingredient in the liquid crystal so that the cosmetically-active or dermatologically-active ingredient penetrates skin at a greater rate than its natural rate; where the transesterified olive oil has been transesterified with cetearyl alcohol and sorbitol.

2. The method of claim 1 where the cosmetically-active or dermatologically-active ingredient is selected from the group consisting of antioxidants, free-radical scavengers, hyaluronic acid, collagen, botulinum toxin, cortison-like drugs, antibiotics, chemotherapeutic agents, wound-healing drugs, and peptides.

3. The method of claim 1 where the cosmetically-active or dermatologically-active ingredient is caffeine.

4. A method of enhancing the skin penetration of a cosmetically-active or dermatologically-active ingredient comprising administering the cosmetically-active or dermatologically-active ingredient to a person in a cosmetic formulation containing a transesterified olive oil and the cosmetically-active or dermatologically-active ingredient where the cosmetic formulation is prepared by:
   (a) emulsifying the transesterified olive oil to form a liquid crystal; and
   (b) embedding the cosmetically-active or dermatologically-active ingredient in the liquid crystal so that the cosmetically-active or dermatologically-active ingredient penetrates skin at a greater rate than its natural rate; where the transesterified olive oil has been transesterified with cetearyl alcohol and sorbitol.

5. The method of claim 4 where the cosmetically-active or dermatologically-active ingredient is selected from the group consisting of antioxidants, free-radical scavengers, hyaluronic acid, collagen, botulinum toxin, cortison-like drugs, antibiotics, chemotherapeutic agents, wound-healing drugs, and peptides.

6. The method of claim 4 where the cosmetically-active or dermatologically-active ingredient is caffeine.

* * * * *